(12) United States Patent
Gallnböck

(10) Patent No.: US 7,753,884 B2
(45) Date of Patent: Jul. 13, 2010

(54) DEVICE FOR THE DOSED DELIVERY OF A FLUID

(75) Inventor: Bernhard Gallnböck, Linz (AT)

(73) Assignee: PRO-MED Medizinische Produktions- und Handels-AG, Linz (AT)

( * ) Notice: Subject to any disclaimer, the term of this patent is extended or adjusted under 35 U.S.C. 154(b) by 804 days.

(21) Appl. No.: 10/567,401

(22) PCT Filed: Aug. 3, 2004

(86) PCT No.: PCT/AT2004/000274

§ 371 (c)(1),
(2), (4) Date: Feb. 3, 2006

(87) PCT Pub. No.: WO2005/011778

PCT Pub. Date: Feb. 10, 2005

(65) Prior Publication Data

US 2006/0255063 A1    Nov. 16, 2006

(30) Foreign Application Priority Data

Aug. 4, 2003   (AT) .............................. A 1224/2003

(51) Int. Cl.
*A61M 37/00* (2006.01)
*B65D 35/56* (2006.01)

(52) U.S. Cl. .......................... 604/147; 222/95; 222/105; 222/386.5; 222/389; 604/131; 604/132; 604/145

(58) Field of Classification Search .................. 222/95, 222/105, 386.5, 389; 604/131–132, 145, 604/147
See application file for complete search history.

(56) References Cited

U.S. PATENT DOCUMENTS

| | | | | |
|---|---|---|---|---|
| 3,504,827 A | * | 4/1970 | Larson | 222/95 |
| 4,090,514 A | * | 5/1978 | Hinck et al. | 604/142 |
| 4,906,103 A | * | 3/1990 | Kao | 366/130 |

(Continued)

FOREIGN PATENT DOCUMENTS

WO       WO 93/07920 A     4/1993

(Continued)

OTHER PUBLICATIONS

International Search Report in English ISA dated Oct. 15, 2004.

*Primary Examiner*—Kevin P Shaver
*Assistant Examiner*—Andrew P Bainbridge
(74) *Attorney, Agent, or Firm*—Collard & Roe, P.C.

(57) ABSTRACT

An apparatus is proposed for the dosed dispensing of a fluid, especially an infusion fluid, comprising a housing (1) with a fluid chamber and a pressure medium chamber (3) by which a flexible wall (4) of the fluid chamber can be pressurized from the outside with a pressure medium. In order to provide a re-useable infusion pump with especially simple means it is proposed that the housing (1) consists of two mutually detachably joined housing parts (6, 7), of which the one comprises the pressure medium chamber (3) and the other receives in an exchangeable manner the fluid chamber configured as a leak-proof infusion bag (2), and that the housing part (6) with the pressure medium chamber (3) is sealed by a membrane (5) against the housing part (7) receiving the infusion bag (2) and is connected to a gas pressure source (11).

1 Claim, 2 Drawing Sheets

U.S. PATENT DOCUMENTS

| | | | |
|---|---|---|---|
| 5,080,652 A * | 1/1992 | Sancoff et al. | 604/132 |
| 5,090,963 A * | 2/1992 | Gross et al. | 604/132 |
| 5,137,175 A * | 8/1992 | Kowalski et al. | 222/1 |
| 5,242,406 A * | 9/1993 | Gross et al. | 604/132 |
| 5,308,335 A * | 5/1994 | Ross et al. | 604/141 |
| 5,421,484 A * | 6/1995 | Beach | 222/95 |
| 5,553,741 A * | 9/1996 | Sancoff et al. | 222/1 |
| 5,558,255 A * | 9/1996 | Sancoff et al. | 222/189.06 |
| 5,571,261 A * | 11/1996 | Sancoff et al. | 222/386.5 |
| 5,680,966 A * | 10/1997 | Johnson | 222/209 |
| 5,891,097 A * | 4/1999 | Saito et al. | 604/141 |
| 6,062,429 A * | 5/2000 | West et al. | 222/95 |
| 6,406,458 B1 * | 6/2002 | Tillander | 604/147 |
| 6,510,965 B1 * | 1/2003 | Decottignies et al. | 222/95 |
| 6,554,164 B1 * | 4/2003 | Jones | 222/105 |
| 6,619,505 B1 * | 9/2003 | Decottignies et al. | 222/95 |
| 6,981,613 B1 * | 1/2006 | Kamisugi | 222/105 |
| 2006/0255063 A1 * | 11/2006 | Gallnbock | 222/95 |

FOREIGN PATENT DOCUMENTS

| | | |
|---|---|---|
| WO | WO 95/23641 A | 9/1995 |
| WO | WO 01/26715 A | 4/2001 |

* cited by examiner

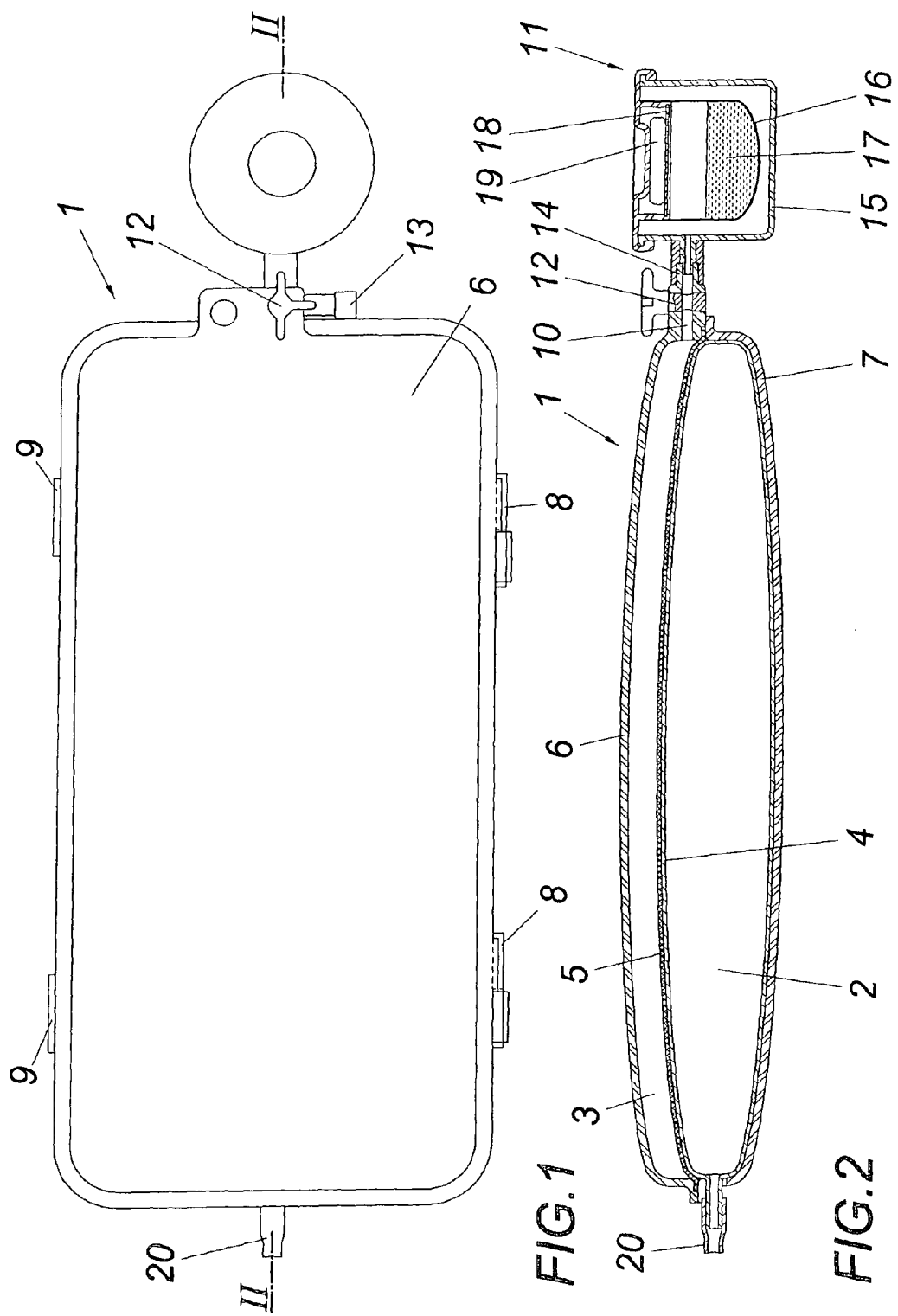

DEVICE FOR THE DOSED DELIVERY OF A FLUID

CROSS REFERENCE TO RELATED APPLICATIONS

Applicant claims priority under 35 U.S.C. §119 of Austrian Application No. A 1224/2003 filed Aug. 4, 2003. Applicant also claims priority under 35 U.S.C. §365 of PCT/AT2004/000274 filed Aug. 3, 2004. The international application under PCT article 21(2) was not published in English.

FIELD OF THE INVENTION

The invention relates to an apparatus for the dosed dispensing of a fluid, especially an infusion fluid, comprising a housing with a fluid chamber and a pressure medium chamber by which a flexible wall of the fluid chamber can be pressurized from the outside with a pressure medium.

DESCRIPTION OF THE PRIOR ART

In such a known apparatus (WO 95/23 641 A1), the fluid chamber, the pressure medium chamber and a gas pressure generator are housed in a common housing. The gas pressure generator consists of a reaction chamber which contains an organic acid, mostly citric acid in the required concentration, and a carbonate preparation, mostly sodium carbonate with binding agents, which is separated from the container by a membrane and is pressed into a tablet. For the purpose of activating the gas pressure generator, the membrane is separated between the acid and the carbonate, whereupon the carbonate reacts with the acid and subsequently releases a reaction gas, mostly carbon dioxide, which is guided via a hydrophobic gas-permeable membrane and a cannula to a pressure medium chamber from where the infusion fluid is pressurized via the flexible wall of the fluid chamber. The infusion speed can be regulated via the gas pressure and/or a control valve in the infusion cannula leading from the apparatus to the patient. Such apparatuses for the dosed dispensing of an infusion fluid come with the advantage that a patient can be supplied with an infusion fluid over a prolonged period at virtually constant pressure, with the patient remaining mobile during the dispensing of the fluid because her or she is able to carry the apparatus on the body. It has proven to be a disadvantage in connection with this known apparatus that it is merely a disposable product which is relatively expensive to produce and needs to be disposed of at increased expense after use.

SUMMARY OF THE INVENTION

The invention is therefore based on the object of providing an apparatus for the dosed dispensing of a fluid, especially an infusion fluid, which can be produced in a cost-effective way, is mostly re-useable and causes only very low operating costs.

This object is achieved by the invention in such a way that the housing consists of two mutually detachably joined parts, of which the one forms the pressure medium chamber and the other receives the fluid chamber configured as a leak-proof infusion bag in an exchangeable manner, and that the housing part with the pressure medium chamber is sealed by a membrane against the housing part receiving the infusion bag and is connected to a gas pressure source.

The invention provides a re-useable apparatus for the dosed dispensing of a fluid in a simple way, such that drugs filled or diluted in infusion bags, or pesticides or fertilizers for plants, can be used in a simple way in the apparatus. Infusion bags of different dimensions and filling quantities can be used in an apparatus in accordance with the invention. Prior to the dosed dispensing of the fluid it is merely necessary to insert the infusion bag into the respective housing part and the two housing parts only need to be joined with each other in a rigid fashion, whereupon the pressure medium chamber can be filled with a pressure medium in such a way that it acts via the membrane directly upon the jacket of the infusion bag and thus ensures the expulsion of the fluid or the infusion fluid from the fluid chamber with the desired pressure. Because the housing part with the pressure medium chamber is sealed by a membrane against the housing part receiving the infusion bag and is connected to a gas pressure source, an especially simple, reliable and re-useable construction of an apparatus in accordance with the invention is obtained, which in addition causes only very low operating costs. The gas pressure source is connected for example to the housing part forming the pressure medium chamber or is inserted into a respective recess formed by the pressure medium chamber, thus leading to especially compact conditions.

One of the two mutually detachably joined housing parts thus receives the pressure medium chamber sealed by a membrane and the other housing part receives the infusion bag, which allows performing a change of the infusion bags in an especially rapid and simple manner. Moreover, it is recommended in accordance with an advantageous embodiment of the invention that the two housing parts are joined in an articulated manner on one side and comprise a latching device on the opposite side, as a result of which the two housing parts can be opened relative to each other, but still remain mutually joined in a non-losing way and can be mutually latched.

Gas pressure generators especially known from WO 95/23641 A1 are especially recommended as gas pressure sources, which are preferably connected via a control and/or pressure reducing valve to the pressure medium chamber in order to ensure the most constant adjustable pressure over the entire dispensing period of the infusion fluid and to enable an interruption of the gas supply to the pressure medium chamber at any time. A conventional pressure relief valve can be provided in the simplest of cases as a pressure reducing valve. For regulating the venting and for resetting the membrane or for diverting the gas when changing the infusion bag or the gas generator, it is advantageous when the gas pressure source remains joined in an exchangeable manner to the control or pressure reducing valve associated with the housing.

BRIEF DESCRIPTION OF THE DRAWINGS

The invention is shown in closer detail by reference to a schematic embodiment, wherein:

FIG. 1 shows an apparatus in accordance with the invention in a top view;

FIG. 2 show the apparatus of FIG. 1 in a sectional view along line II-II, and

DESCRIPTION OF THE PREFERRED EMBODIMENTS

Figure 3:
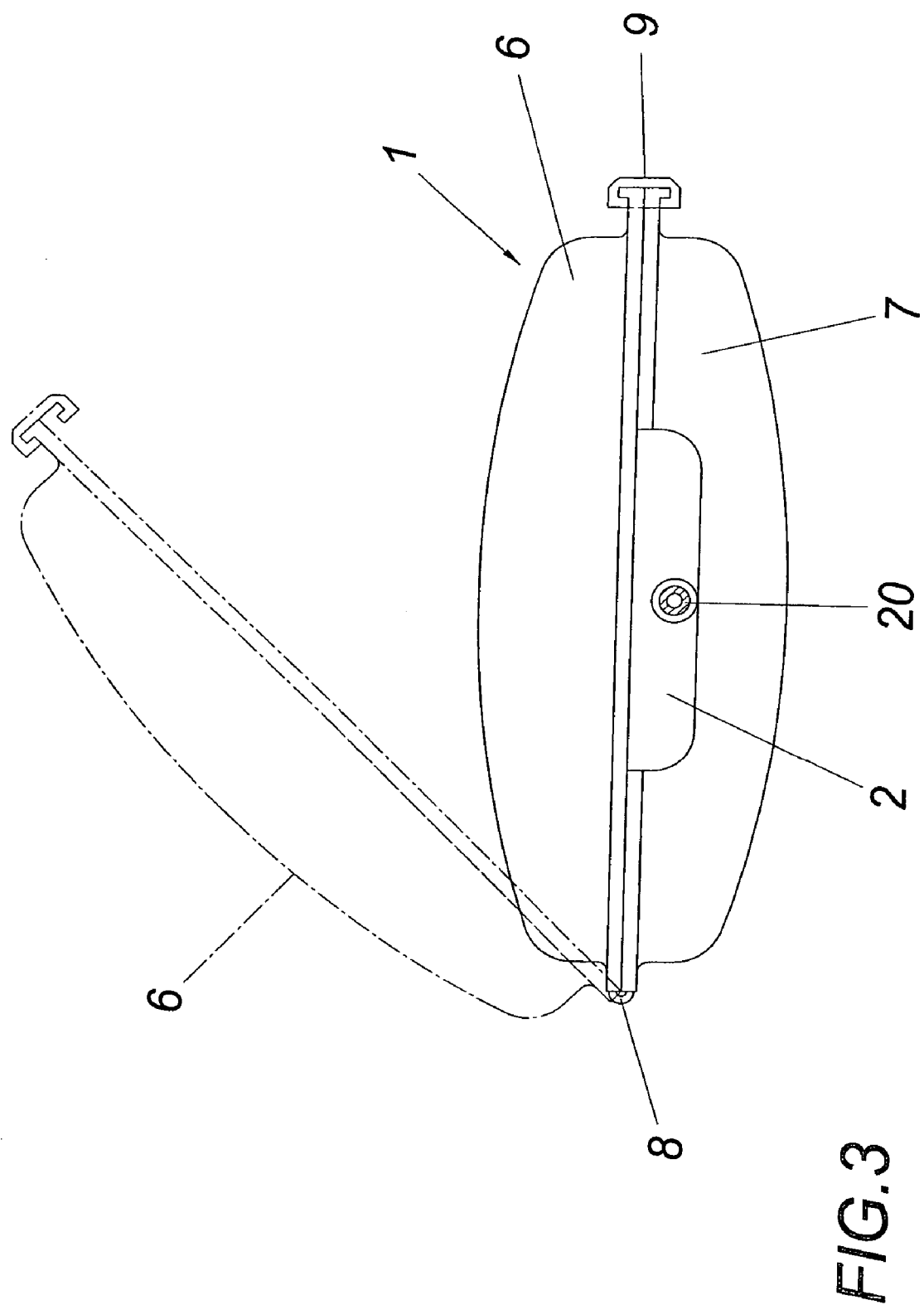
FIG. 3 shows the apparatus of FIGS. 1 and 2 in a front view.

An apparatus in accordance with the invention for the dosed dispensing of an infusion fluid comprises a housing 1 which receives a flexible fluid chamber in the form of an infusion bag 2 and a pressure medium chamber 3, through which a flexible wall 4 of the infusion bag 2 can be pressurized with a pressure medium from the outside via a membrane 5. The housing 1 consists of two housing parts 6, 7 which are joined in an articulated manner with each other on one side by means of two hinge joints 8 and comprises on the opposite side a latching device 9 with which the two housing parts 6, 7 can be fixed in their position in a mutually closed position with respect to each other.

In connection with the two detachably connected housing parts 6, 7, the one housing part 6 receives in an exchangeable manner the pressure medium chamber 3 and the other housing part 7 the leak-proof infusion bag 2. The housing part 6 with the pressure medium chamber 3 is sealed by membrane 5 relative to the housing part 7 receiving the infusion bag 2 and is connected via a duct 10 to an exchangeable gas pressure source 11. The membrane is glued or welded together with the associated housing part 6 in the region of the separating plane of the two housing parts 6, 7. A control valve 12 and pressure reducing valve 13 are arranged between the gas pressure source 11 and the pressure medium chamber 3 with which the gas supply from the gas pressure source 11 to the pressure medium chamber 3 can be controlled or regulated and the gas pressure can be limited to a pre-adjustable maximum value. Since after the use of the apparatus in accordance with the invention it is merely necessary to exchange the gas pressure source 11 and the infusion bag 2 and the remaining apparatus can be re-used, the gas pressure source 11 is connected in an exchangeable manner via a plug-in coupling 14 with the control valve 12 which is associated with housing 1.

The gas pressure source 11 consists of a container 15 with a hydrophobic gas-permeable membrane 16 which receives an organic acid 17, especially citric acid, in the required concentration and of a carbonate preparation, especially sodium carbonate with binding agents, which is separated from the acid 17 by way of a film 18 or the like and is pressed into a tablet 19.

For the purpose of using the apparatus in accordance with the invention, an infusion bag 2 is placed in the opened housing 1 (see FIG. 3), with the infusion cannula 20 being closed by means of a clip (not shown) and thereafter the housing part 6 receiving the pressure medium chamber 3 is locked with the housing part 7 receiving the infusion bag 2. Thereafter the gas pressure source 11 is activated in such a way that the tablet 19 is brought into contact with the acid 17 by destroying the film 18, whereupon the pressure medium, especially carbon dioxide, is produced as a result of the subsequently occurring chemical reaction. The gas-permeable membrane 16 ensures that merely gases reach the pressure medium chamber 3 and the fluids are held back in the container 15. The gas pressure source 11 is principally determined for single use. Under certain circumstances it is possible to infuse several infusion bags in direct succession with the same gas pressure source 11. This depends on the bag volume and infusion speed. After the start of the reaction in the gas pressure source 11, the gas is introduced from the container 15 via the control valve 12 into the pressure medium chamber 3 where the membrane 5 sits close against the flexible wall 4 of the infusion bag 2 and pressurizes the infusion fluid contained in the infusion bag 2 with the desired pressure for expelling the infusion liquid from the infusion bag 2 through the infusion cannula 20. After the completion of the infusion process, the infusion bag 2 can be removed from the opened housing 1 and be disposed of. The gas pressure source 11 can be removed from the housing 1, whereupon the membrane 5 is reverted back to its starting position when the control valve 12 is opened. The apparatus in accordance with the invention is ready for renewed operation after the insertion of a new infusion bag 2 into the housing 1 and the attachment of a new gas pressure source.

The invention claimed is:

1. An apparatus for dosed dispensing of an infusion fluid comprising:
    (a) a housing comprising detachably-interconnected first and second housing parts, said first housing part comprising a pressurized medium chamber and a first valve selected from the group consisting of a control valve and a pressure reduction valve;
    (b) a fluid-tight infusion bag forming an interchangeable fluid chamber having a flexible wall received within the second housing part;
    (c) a membrane having a first end and a second end, said first and second ends being attached to the housing in a region of a separation plane of the first and second housing parts sealing off the first housing part froth the second housing part;
    (d) a pressurized gas source replaceably connected to the first valve for supplying pressurized gas to the pressurized medium chamber for pressurizing said flexible wall via the membrane, said pressurized gas source comprising a carbonate formulation pressed into a tablet and an organic acid; and
    (e) a plug-in coupling for replaceably connecting the pressurized gas source with the first valve;
    wherein the first valve is directly connected to the pressurized medium chamber; and
    wherein the first and second housing parts are joined to each other at one side in an articulated manner and comprise a latching device on the opposite side.

* * * * *